(12) United States Patent
Kitabayashi

(10) Patent No.: US 7,611,859 B2
(45) Date of Patent: Nov. 3, 2009

(54) METHOD FOR IMPROVING HEAT STABILITY OF COMPOSITION CONTAINING WATER-SOLUBLE COENZYME-BOUND GLUCOSE DEHYDROGENASE (GDH)

(75) Inventor: Masao Kitabayashi, Tsuruga (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 11/392,000

(22) Filed: Mar. 29, 2006

(65) Prior Publication Data

US 2007/0105175 A1    May 10, 2007

Related U.S. Application Data

(60) Provisional application No. 60/736,009, filed on Nov. 10, 2005.

(51) Int. Cl.
*C12Q 1/54* (2006.01)
*A61B 5/00* (2006.01)

(52) U.S. Cl. .......... 435/14; 600/316
(58) Field of Classification Search ......... 435/14; 600/316
See application file for complete search history.

(56) References Cited

U.S. PATENT DOCUMENTS

| | | | |
|---|---|---|---|
| 3,964,974 A | 6/1976 | Banauch et al. | |
| 4,120,755 A | 10/1978 | Pierre et al. | |
| 6,773,564 B1 * | 8/2004 | Yugawa et al. | 204/403.14 |
| 2004/0191883 A1 | 9/2004 | Sode et al. | |
| 2006/0063217 A1 * | 3/2006 | Omura et al. | 435/14 |

FOREIGN PATENT DOCUMENTS

| | | |
|---|---|---|
| EP | 0 992 589 A2 | 4/2000 |
| EP | 1 146 332 A1 | 10/2001 |
| EP | 1 584 675 A1 | 10/2005 |
| JP | 2004-236665 A | 8/2004 |
| JP | 2007-116936 A | 5/2007 |
| WO | WO 02/072839 A1 | 9/2002 |

OTHER PUBLICATIONS

Marini et al., Cell. Mol. Life Sci., 62, 3092-3099, 2005.*
Igarashi et al., *Archives of Biochemistry and Biophysics*, 428: 52-63 (2004).
Takahashi et al., *Proceedings of the Voice I/O Systems Applications Conference*, 68(11): 907-911 (2000).
Smirnoff et al., *Vegetation*, 62: 273-278 (1985).
Asahi Chemical Industry Co., Ltd., "Asahi Chemical Diagnostic Enzymes" (Jun. 1997), pp. 104-106.
Hudson et al., *Biochem. J.*, 273: 645-650 (1991).
Shibuya et al., *Biosci. Biotech. Biochem.*, 61(4): 592-598 (1997).
Toyobo Co., Ltd., "Toyobo Enzymes" (Mar. 1, 1993), pp. 43, 47, 51, 55, 59, 67, 79, 83, 115, 119, 123, 135, 163, 183, 195, 199, 203, 267, 279, and 293.
Wiseman et al., *Biochimica et Biophysica Acta*, 250: 1-5 (1971).
Chang et al., *Biotechnol. Appl. Biochem.*, 22: 203-214 (1995).

* cited by examiner

*Primary Examiner*—Maryam Monshipouri
(74) *Attorney, Agent, or Firm*—Leydig, Voit & Mayer, Ltd.

(57) ABSTRACT

The invention relates to a method for improving the heat stability of glucose dehydrogenase (GDH), comprising a step of combining, in a composition comprising soluble coenzyme-bound glucose dehydrogenase (GDH), the enzyme with any one or more selected from the group consisting of sugar alcohols, carboxyl group-containing compounds, alkali metal-containing compounds, alkali earth metal compounds, ammonium salts, sulfate salts and proteins, thereby improving the heat stability of GDH over that achieved without the inclusion of the compounds.

6 Claims, 1 Drawing Sheet

METHOD FOR IMPROVING HEAT STABILITY OF COMPOSITION CONTAINING WATER-SOLUBLE COENZYME-BOUND GLUCOSE DEHYDROGENASE (GDH)

CROSS-REFERENCE TO RELATED APPLICATION

This patent application claims the benefit of U.S. Provisional Patent Application No. 60/736,009, filed Nov. 10, 2005.

FIELD OF THE INVENTION

The present invention relates to a method for improving the heat stability of a composition comprising water-soluble coenzyme-bound glucose dehydrogenase (glucose dehydrogenase sometimes called "GDH" herein), including glucose dehydrogenase having a flavin compound as its coenzyme.

BACKGROUND OF THE INVENTION

Blood glucose self-measurement is important for diabetes patients to constantly assess their own blood glucose levels and used them in treatment. Enzymes having glucose as a substrate are employed in the monitors used for blood glucose self-measurement. One example of such an enzyme is glucose oxidase (EC 1.1.3.4). Glucose oxidase has long been used as the enzyme in blood glucose monitors because of its high specificity for glucose and excellent heat stability, and the first report actually dates back about 40 years. In blood glucose monitors using glucose oxidase, measurement is accomplished by means of electrons generated as glucose is oxidized and converted to D-glucono-δ-lactone, which are transferred to an electrode via a mediator, but because protons produced during the reaction are likely to be transferred to oxygen, the measurement results are affected by dissolved oxygen.

To avoid this problem NAD(P)-dependent glucose dehydrogenase (EC 1.1.1.47) or pyrroloquinoline quinone (abbreviated herein as PQQ)-dependent glucose dehydrogenase (EC 1.1.5.2 (formerly EC 1.1.99.17) is used as the enzyme in blood glucose monitors. These are superior in that they are not affected by dissolved oxygen, but the former NAD(P)-dependent glucose dehydrogenase (sometimes abbreviated herein as NADGDH) is complicated by poor stability and the need for addition of a coenzyme. On the other hand, PQQ-dependent glucose dehydrogenase (sometimes abbreviated herein as PQQGDH) has poor substrate specificity and acts on sugars other than glucose such as maltose and lactose, detracting from measurement accuracy.

*Aspergillus*-derived flavin-bound glucose dehydrogenase (sometimes abbreviated hereunder as FADGDH) is disclosed in WO 2004-058958. This enzyme is superior in that it has excellent substrate specificity and is not affected by dissolved oxygen. In terms of heat stability, it has an activity survival rate of about 89% following 15 minutes of treatment at 50° C. This stability is still inadequate however considering that heat treatment may be required in some cases in the process of preparing a sensor chip.

SUMMARY OF THE INVENTION

It is an object of the present invention to overcome the difficulties of heat stability that occur with the aforementioned conventional enzymes for blood glucose monitors, and to provide a composition which can be used in practical situations as a reagent for measuring blood glucose.

From previous studies of PQQGDH the inventors have obtained several multiple variants of this enzyme with improved substrate specificity, but some of these variants have poorer heat stability than the wild-type PQQGDH. After exhaustive research aimed at discovering the cause of this problem, it was found that the three-dimensional structure of PQQGDH could be stabilized and its stability improved by adding a certain kind of compound to the enzyme as described in this patent.

After further study, the inventors perfected the present invention upon discovering that similar effects could be achieved for FADGDH and NADGDH.

Strategies for improving the stability of PQQGDH have already been reported in WO 02/072839, which reports on a study using a means of modifying PQQGDH on the genetic level, but the possibility of a means of increasing the stability of an enzyme without modifying it has not heretofore been mentioned.

The inventors also discovered as a result of exhaustive research that a level of heat stability high enough to allow the composition to be heat dried could be achieved by maintaining the pH of a composition comprising GDH and a flavin compound at a pH in the acid range.

A level of heat stability which allows heat drying is a level at which the active survival rate is 10% or more, or preferably 45% or more, or still more preferably 70% or more after 15 minutes of treatment at 50° C.

Taking a different perspective from previous studies, the inventors searched for strategies for more easily improving heat stability, and finally perfected the present invention after further exhaustive research when they showed that the overall stability of a composition comprising GDH could be improved by using a composition with a pH in the acid range and by including one or more dicarboxylic acids or salt compounds.

That is, the present invention consists of the following.

[Item 1] A method for improving the heat stability of glucose dehydrogenase (GDH), comprising the step of combining, in a composition comprising soluble coenzyme-bound glucose dehydrogenase (GDH), the enzyme with any one or more selected from the group consisting of sugar alcohols, carboxyl group-containing compounds, alkali metal-containing compounds, alkaline earth metal compounds, ammonium salts, sulfate salts and proteins, thereby improving the heat stability of GDH over that achieved without the inclusion of the compounds.

[Item 2] The method for improving heat stability according to Item 1, wherein the coenzyme is pyrroloquinoline quinone, a flavin compound or nicotinamide adenine dinucleotide (NAD).

[Item 3] The method for improving heat stability according to Item 1, wherein the final concentration of each included compound is 0.1% or more.

[Item 4] The method for improving heat stability according to any of Items 1 through 3, wherein the added compound is any one or more selected from the group consisting of mannitol, inositol, arabitol, adonitol, galactitol, valine, histidine, phenylalanine, leucine, calcium glycerate, succinic acid, potassium chloride, ammonium chloride, diammonium hydrogen citrate, fumaric acid, malonic acid, pimelic acid, 3-3'dimethylglutaric acid, lysine, phthalic acid, maleic acid, glutaric acid, ammonium sulfate, sodium sulfate, sodium chloride and bovine serum albumin (BSA).

[Item 5] A composition comprising soluble coenzyme-bound glucose dehydrogenase the heat stability of which is improved by the method according to any of Items 1 through 4.

[Item 6] A method for measuring a glucose concentration using the composition according to Item 5.

[Item 7] A glucose sensor comprising the composition according to Item 5.

[Item 8] A method for manufacturing a composition comprising glucose dehydrogenase (GDH) with improved heat stability, comprising the step of combining, in a composition comprising soluble coenzyme-bound glucose dehydrogenase (GDH), the enzyme with any one or more selected from the group consisting of sugar alcohols, carboxyl group-containing compounds, alkali metal-containing compounds, alkaline earth metal compounds, ammonium salts, sulfate salts and proteins, thereby improving the heat stability of GDH over that achieved without the inclusion of the compounds.

[Item 9] A method for improving the heat stability of a composition comprising soluble coenzyme-bound glucose dehydrogenase (GDH), comprising the step of maintaining the pH of the composition in the acid range of less than pH 7, thereby improving the heat stability of the composition over that achieved with the composition at a pH of 7.3.

[Item 10] A method for improving the heat stability of a composition comprising soluble coenzyme-bound glucose dehydrogenase (GDH), comprising the step of maintaining the pH of the composition at pH 3.1 to 7.0, thereby improving the heat stability of the composition over that achieved with the composition at a pH of 7.4.

[Item 11] The method for improving the heat stability of a composition according to Item 9 or 10, wherein the soluble coenzyme-bound glucose dehydrogenase (GDH) is glucose dehydrogenase (GDH) having a flavin compound as its coenzyme.

[Item 12] The method for improving heat stability according to Item 11, wherein the glucose dehydrogenase (GDH) having a flavin compound as its coenzyme is derived from a filamentous fungi.

[Item 13] A composition the heat stability of which is improved by the method according to any of Items 9 through 12.

[Item 14] The GDH-containing composition according to Item 13, wherein in a composition comprising soluble coenzyme-bound glucose dehydrogenase (GDH), GDH activity even after 15 minutes of treatment at 50° C. is 10% or more of the GDH activity of the composition stored at 4° C.

[Item 15] The GDH-containing composition according to Item 13, wherein in a composition containing glucose dehydrogenase (GDH) having a flavin compound as its coenzyme, GDH activity even after 15 minutes of treatment at 50° C. is 45% or more of the GDH activity of the composition stored at 4° C.

[Item 16] The composition according to Item 13, containing one or more dicarboxylic acids or salt compounds.

[Item 17] The composition according to Item 13, containing one or more of the compounds of sodium chloride, sodium sulfate, trisodium citrate, ammonium sulfate, succinic acid, malonic acid, glutaric acid, phthalic acid and maleic acid.

[Item 18] A method for measuring a glucose concentration using the composition according to Item 13.

[Item 19] A glucose sensor comprising the composition according to Item 13.

[Item 20] A method for manufacturing a composition comprising soluble coenzyme-bound glucose dehydrogenase (GDH) in which heat stability is improved, comprising the step of maintaining the pH of the composition in the acid range of pH 7 or less, thereby improving the heat stability of the composition over that achieved with the composition at a pH of 7.3.

[Item 21] A method for manufacturing a composition comprising soluble coenzyme-bound glucose dehydrogenase (GDH) in which heat stability is improved, comprising the step of maintaining the pH of the composition at pH 3.1 to 7.0, thereby improving the heat stability of the composition over that achieved with the composition at a pH of 7.4.

The improvement in heat stability achieved by the present invention makes it possible to reduce thermal deactivation of the enzyme during preparation of the glucose measurement reagent, glucose assay kit and glucose monitor, and to reduce the amount of the enzyme used and improve measurement accuracy. Moreover it also makes it possible to provide a reagent for measuring blood glucose using GDH having excellent storage stability.

DETAILED DESCRIPTION OF THE INVENTION

Figure 1:
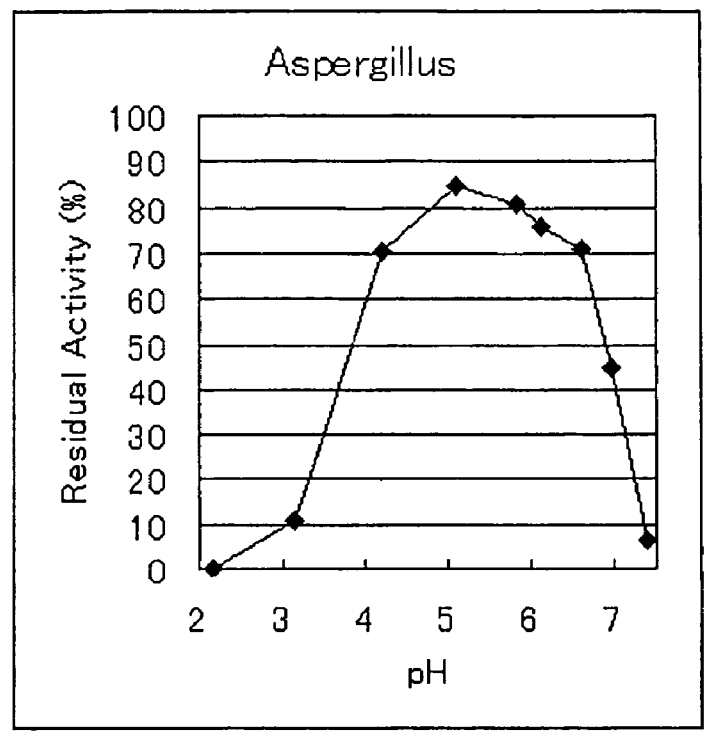
FIG. 1 shows the pH dependence of heat stability of FADGDH derived from an *Aspergillus terreus* subspecies.

The present invention is explained in more detail below.

GDH is an enzyme that catalyzes the following reaction:

D-glucose+electron-transferring substance (oxide form)→ D-glucono-δ-lactone+electron-transferring substance (reduced form).

It is an enzyme which catalyzes a reaction in which D-glucose is oxidized to produced D-glucono-1,5-lactone, with no particular limits on its derivation or structure.

There are no particular limits on what GDH can be used in the method of the present invention as long as it is soluble coenzyme-bound glucose dehydrogenase (GDH).

Coenzymes that can be used include for example pyrroloquinoline quinone, flavin compounds, nicotinamide adenine dinucleotide (NAD) and the like.

There are no particular limits on the GDH having pyrroloquinoline quinone as its coenzyme (PQQGDH) that can be used in the present invention, but examples include those derived from microorganisms such as *Acinetobacter calcoaceticus* LMD 79.41 (A.M. Cleton-Jansen et al, *J. Bacteriol.* 170, 2121 (1988) and *Mol. Gen. Genet.* 217, 430 (1989)), *Escherichia coli* (A.M. Cleton-Jansen et al, *J. Bacteriol.* 172, 6308 (1990)) and *Gluconobacter oxydans* (*Mol. Gen. Genet.* 229, 206 (1991)), and that derived from the *Acinetobacter baumanni* NCIMB11517 reported in WO 2004/058958.

However, it is difficult to modify the membrane enzymes found in *Escherichia coli* to make them soluble, so soluble PQQGDH derived from *Acinetobacter calcoaceticus* or *Acinetobacter baumanni* is preferably selected.

The *Acinetobacter baumanni* NCIMB11517 strain was previously classified into *Acinetobacter calcoaceticus*.

GLD-321 produced by Toyo Boseki K.K. and other commercial products can be used for these PQQGDH enzymes. Alternatively, they can be easily manufactured by a person skilled in the art using known techniques in the field.

There are no particular limits on the GDH having FAD as its coenzyme (FAD-bound GDH) that can be used in the present invention, but examples include those derived from microorganisms such as *Penicillium, Aspergillus* and the like. These microbial strains can be easily obtained by means of a request to a depository authority. For example, in the *Penicillium* genus *Penicillium lilacinoechinulatum* is recorded at the Biological Resource Center of the National Institute of Technology and Evaluation under Accession No. NBRC6231.

There are no particular limits on the GDH having NAD as its coenzyme that can be used in the present invention, but a commercial product (GLD-311) sold by Toyo Boseki can be obtained and used. It can also be prepared by a variety of known methods.

GDH having some of the amino acid residues deleted or replaced or other amino acid residues added in the examples given above can still be used as GDH in the present invention as long as glucose dehydrogenase activity is retained.

Such modification can easily be performed by the skilled artisan according to known techniques in the art. A variety of methods for introducing a site-directed mutagenesis to a protein by substituting or inserting one or more bases to a nucleotide sequence of a gene coding for the protein are disclosed in Sambrook et al, Molecular Cloning; A Laboratory Manual $2^{nd}$ Eddition(1989)Cold Spring Harbor Laboratory Press, New York. For example, naturally-occurring microorganisms producing the GDH, or transformant prepared by inserting a naturally-occurring or modified GDH gene into an expression vector (a variety of vectors including a plasmid are known), followed by transforming a suitable host (a variety of hosts including *E. coli* are known) with the expression vector, are cultured, host cells are collected from a culture medium by centrifugation, cells are broken down mechanically or enzymatically with lysozyme, optionally solubilized by the addition of a chelating agent such as EDTA or a surfactant to obtain a water soluble fraction containing GDH. The expressed GDH can be secreted to a culture medium using a suitable host-vector system.

GDH can be separated and precipitated from the GDH-containing solution by concentration under reduced pressure, membrane concentration, salting out using ammonium sulfate or sodium sulfate, or a fractional precipitation with a hydrophilic solvent such as methanol, ethanol, acetone, etc. Heat treatment and isoelectric treatment are also an effective purification method. Purified GDH can be obtained by gel filtration with adsorbent or gel filtering agent, adsorption chromatography or affinity chromatography. The standard enzyme is preferably purified enough to show a single band in electrophoresis (SDS-PAGE).

The PQQGDH can be heat-treated at 25 to 50° C., preferable 30 to 45° C. to increase a proportion of holoenzyme to the total GDH protein before or after the above-mentioned steps.

Concentration of PQQGDH of the invention is not specifically limited.

The appropriate range differs depending on the properties and the like of the enzyme used, but for practical purposes the concentration is one at which a person skilled in the art could measure glucose with adequate reliability using the enzyme.

For example, the concentration of PQQGDH in the present invention is not particularly restricted, but in solution it is preferably 0.1 to 100 U/mL or more preferably 1 to 50 U/mL or still more preferably 2 to 10 U/mL. A similar concentration is also desirable in a powder or freeze-dried product, but a concentration of 100 U/mL or more can also be used when preparing a powder sample.

The concentration of NADGDH in the present invention is also not particularly restricted, but in solution it is preferably 10 to 1000 U/mL or more preferably 20 to 500 U/mL or still more preferably 50 to 150 U/mL. A similar concentration is also desirable in a powder or freeze-dried product, but a concentration of 1000 U/mL or more can also be used when preparing a powder sample.

The concentration of the FADGDH in the present invention is also not particularly restricted but in solution it is preferably 0.01 to 100 U/mL or more preferably 0.1 to 50 U/mL or still more preferably 0.2 to 10 U/mL. A similar concentration is also desirable in a powder or freeze-dried product, but a concentration of 100 U/mL or more can also be used when preparing a powder sample.

There are no particular limits on the medium for culturing the aforementioned microorganism as long as it is one in which the microorganism can grow and produce the GDH described in the present invention, but preferably it is one containing the necessary carbon sources, inorganic nitrogen sources and/or organic nitrogen sources necessary for the microorganism to grow, and still more preferably it is a liquid medium suited to aeration-agitation. In the case of a liquid medium, examples of carbon sources include glucose, dextran, soluble starch, sucrose and the like while examples of nitrogen sources include ammonium salts, nitrate salts, amino acids, corn steep liquor, peptone, casein, meat extract, defatted soy beans, potato extract and the like. Other nutrient sources (such as calcium chloride, sodium hydrogen phosphate, magnesium chloride and other inorganic salts, vitamins and the like) can also be included as desired.

Culture is by ordinary methods known in the field. For example, spores or growing cells of the microorganism are seeded in liquid medium comprising the aforementioned nutrients, and the bacteria can be made to proliferate by stationary culture or aeration-agitation, but an aeration-agitation culture is preferred. The pH of the culture liquid is preferably 5 to 9 or more preferably 6 to 8. The temperature is normally 14 to 42° C. or preferably 20 to 40° C. Culture is normally continued for 14 to 144 hours, and is preferably terminated at the point at which the level of GDH expression peaks under each set of culture conditions. To determine this point, the culture liquid can be sampled and GDH activity in the culture liquid measured to monitor changes, and once GDH activity ceases to rise over time it is considered to have peaked and culture is terminated.

As a method of extracting GDH from the aforementioned culture liquid, to collect GDH which has accumulated inside the cells the cells alone can by collected by centrifugation, filtration or the like, and re-suspended in a solvent, preferably water or buffer solution. The re-suspended cells can be disrupted by known means and the GDH in the cells collected in the solvent. The cells can be disrupted using a bacteriolytic enzyme or by mechanical means. There are no particular limits on the bacteriolytic enzyme as long as it has the ability to eliminate bacterial cell walls, but one enzyme that can be used is "Lyticase" (Sigma). Means of physical disruption include ultrasound, glass beads, french press and the like. After disruption the solution can be centrifuged or filtered and the residue removed to obtain a raw GDH extract solution.

Culture in the present invention can also be by solid culture. Eukaryotic microorganisms capable of producing the GDH of the present invention are preferably grown on wheat or other bran with the temperature, humidity and the like controlled appropriately. In this case, the culture may be stationary or the culture may be mixed by agitation or the like. GDH is extracted by adding a solvent, preferably water or buffer solution, to the culture to dissolve the GDH, and separating the cells from the bran or other solid matter by centrifugation of filtration.

The GDH can be purified by a combination of various commonly used separation techniques suited to the fraction having GDH activity. A known method such as salting out, solvent precipitation, dialysis, ultrafiltration, gel filtration, unmodified PAGE, SDS-PAGE, ion-exchange chromatography, hydroxyapatite chromatography, affinity chromatography, reverse-phase high-speed liquid chromatography, isoelectric focusing or the like can be selected appropriately for separation from the aforementioned GDH extract.

One mode of the method for improving the heat stability of GDH of the present invention comprises a step of combining, in a composition comprising soluble coenzyme-bound glucose dehydrogenase (GDH), (1) the enzyme and (2) one or more compounds selected from a group consisting of sugar alcohols, carboxyl group-containing compounds, alkali metal-containing compounds, alkali earth metal compounds, ammonium salts, sulfate salts and proteins.

Desirable examples of the compound to be added include one or more selected from a group consisting of mannitol, inositol, arabitol, adonitol, galactitol, valine, histidine, phenylalanine, leucine, calcium glycerate, succinic acid, potassium chloride, ammonium chloride, diammonium hydrogen citrate, fumaric acid, malonic acid, pimelic acid, 3-3'-dimethylglutaric acid, lysine, phthalic acid, maleic acid, glutaric acid, ammonium sulfate, sodium sulfate, sodium chloride and bovine serum albumin (BSA).

There are no particular limits on the concentration of these compounds to be included, but in solution it is preferably 0.001 to 30% or more preferably 0.01 to 5% or still more preferably 0.01 to 1% by weight. A similar concentration is desirable in the case of a powder or freeze-dried product, but in the case of a powder or freeze-dried product the same effects can be achieved through addition of a lower concentration than in the case of a solution.

The concentrations of the compounds described in the examples are final concentrations of the compounds combined and stored with the GDH enzyme. Examples of desirable combinations include a combination with a salt compound having similar properties and a combination of different carboxylic acid-containing compounds, and for example the effects of a salt compound and a carboxylic acid-containing compound reinforce one another when the two are combined.

The pH of the composition can be maintained in the acid range of pH 7 or less in order to further improve heat stability in the aforementioned mode. Alternatively, a dicarboxylic acid such as succinic acid, malonic acid, glutaric acid, phthalic acid or maleic acid or a salt compound such as sodium chloride, sodium sulfate, trisodium citrate or ammonium sulfate can be included.

A different mode of the method for improving the heat stability of GDH of the present invention is a method of improving the heat stability of the composition over that achieved at pH 7.3 or more, comprising a step of maintaining the pH of the composition in the acid range of pH 7 or less in a composition comprising soluble coenzyme-bound glucose dehydrogenase (GDH).

Yet another mode of the method for improving the heat stability of the GDH of the present invention is a method of improving the heat stability of the composition over that achieved at pH 7.4, comprising a step of maintaining pH of the composition at pH 3.1 to 7.0 in a composition comprising soluble coenzyme-bound glucose dehydrogenase (GDH).

The pH is preferably 3.1 to 7.0 or more preferably 4.0 to 6.5 or still more preferably 4.0 to 6.0.

Even after being treated for 15 minutes at 50° C., the aforementioned composition retains GDH activity equal to 10% or more of the GDH activity of the same composition stored at 4° C. In the case of a composition comprising glucose dehydrogenase (GDH) having a flavin compound as the coenzyme, even after 15 minutes of treatment at 50° C. the composition retains GDH activity equal to 45% or more of the GDH activity of the same composition stored at 4° C.

In this mode, the composition preferably contains one or more dicarboxylic acids or salt compounds. Examples of dicarboxylic acids include succinic acid, malonic acid, glutaric acid, phthalic acid and maleic acid, while examples of salt compound include sodium chloride, sodium sulfate, trisodium citrate, ammonium sulfate and the like. One or more of these compounds can be included in the present invention.

There are no particular limits on the concentrations of these compounds to be included, but in solution it is preferably 1 mM to 10 M or more preferably 5 mM to 5 M or still more preferably 20 mM to 1 M. When preparing a powder or freeze-dried product, a freeze-dried sample with the same effects can be obtained by freeze drying a composition containing the compound in the same concentration as in the solution.

The concentrations of the compounds described in the examples are final concentrations of the compounds combined and stored with the GDH enzyme. Examples of desirable combinations include a combination with a salt compound having similar properties and a combination of different carboxylic acid-containing compounds, and for example it is desirable to combine a salt compound with a carboxylic acid-containing compound because the effects of the two reinforce one another in combination.

A sugar alcohol, carboxylic group-containing compound, alkali metal-containing compound, alkali earth metal compound, ammonium salt, sulfuric acid salt or protein such as mannitol, inositol, arabitol, adonitol, galactitol, valine, histidine, phenylalanine, leucine, calcium glycerate, succinic acid, potassium chloride, ammonium chloride, diammonium hydrogen citrate, fumaric acid, malonic acid, pimelic acid, 3-3'dimethylglutaric acid, lysine, phthalic acid, maleic acid, glutaric acid, ammonium sulfate, sodium sulfate, sodium chloride, bovine serum albumin (BSA) or the like can be included to further improve the heat stability in this mode.

The composition comprising GDH of the present invention can be provided in liquid form or can be made into a powder by freeze drying, vacuum drying, spray drying or the like. In this case, the GDH can be dissolved in a buffer or the like for purposes of use, and sugars, sugar alcohols, amino acids, proteins, peptides and the like other than the aforementioned compounds used in the aforementioned invention can also be added as excipients, stabilizers and the like. The resulting powder can also be granulated. Examples of such substances include trehalose, sucrose, sorbitol, erythritol, glycerol and other sugars and sugar alcohols, glutamic acid, alginic acid and other amino acids and bovine serum albumin, egg white albumin, and various chaperones and other proteins and peptides.

There are no particular limits on the compositions of the buffers used in extracting, refining and powdering the GDH as described above or in stability testing, but preferably they have buffering ability in the pH range of 5 to 8, and examples include buffers such as boric acid, tris-hydrochloric acid and potassium phosphate and Good buffers such as BES, Bicine, Bis-Tris, CHES, EPPS, HEPES, HEPPSO, MES, MOPS, MOPSO, PIPES, POPSO, TAPS, TAPSO, TES and Tricine.

One or two or more of these can be used. A compound of one or more including those other than the above can also be used.

There are no particular limits on the added concentrations of these within the range having buffering ability, but the upper limit is preferably 100 mM or less or more preferably 50 mM or less, and the lower limit is preferably 5 mM or more.

The content of a buffer in a powder or freeze-dried product is not particularly limited but should be in the range of preferably 0.1% or more or more preferably 0.1 to 30% (weight ratio).

A variety of commercial reagents can be used for these.

The various compounds describe above can be added at the time of measurement or can be included in advance when preparing the glucose measurement reagent, glucose assay kit or glucose sensor as described below. They can also be added to the process liquid at any of the various manufacturing steps for extracting, purification, powdering and the like of the GDH. Regardless of the form, whether liquid, dried or the like, they should be able to function during measurement.

Improving heat stability in the present invention means increasing the survival rate (%) of the GDH enzyme maintained after a composition comprising the GDH enzyme has been heat treated for a fixed time at a fixed temperature. In the invention of this application, the survival rate of a sample stored at 4° C., at which almost complete activity is retained, is given as 100%, and the survival rate of the enzyme is calculated by comparing this with the activity rate of a GDH solution which has been heat treated for a fixed time at a fixed temperature. If the survival rate is higher than without addition of the compound, the heat stability of GDH is judged to have been improved.

Specifically, improvements in stability were evaluated as follows.

The GDH activity value (a) of a solution stored at 4° C. and the GDH activity value (b) after heat treatment for a fixed time at a fixed temperature were measured by the methods described below for measuring GDH enzyme activity, and the relative value ((b)/(a)×100) was calculated given 100 as measurement value (a). This relative value was the survival rate (%). If the survival rate was greater with the compound added than without, heat stability was judged to have been improved.

The effects of the present invention are more conspicuous in a system comprising a mediator. There are no particular limits on the mediator than can be used in the method of the present invention, but examples include a combination of phenazine methosulfate (PMS) with 2,6-dichlorophenol-indophenol (DCPIP), a combination of PMS with nitroblue tetrazolium (NBT), DCPIP alone, ferricyanide ions alone (with potassium ferricyanide for example as the compound) and ferrocene alone. Of these, ferricyanide ions (with potassium ferricyanide or the like as the compound) are preferred.

Because these mediators differ in terms of sensitivity, the added concentration does not need to be determined exactly, but generally it is desirable to add 1 mM or more.

These mediators may be added during measurement or may be included in advance during preparation of the glucose measurement reagent, glucose assay kit or glucose sensor as described below. In this case, regardless of the state, whether liquid, dried or the like, they should be dissociated to produce ions during the measurement reaction.

A variety of components can also be included in the present invention as necessary. For example, surfactants, stabilizers, excipients and the like can be added.

For example, one or two or more amino acids can be selected from the group consisting of glutamic acid, glutamine and lysine. Bovine serum albumin (BSA), egg white albumin (OVA) and the like can also be included.

In the case of PQQGDH, the PQQGDH can be further stabilized by the addition of calcium ions or salts thereof and glutamic acid, glutamine, lysine and other amino acids as well as serum albumin and the like.

For example, PQQGDH can be stabilized by including calcium ions or calcium salts. Examples of calcium salts include calcium chloride and calcium acetate, calcium citrate and other calcium salts of inorganic or organic acids. In an aqueous composition, the content of calcium ions is preferably $1 \times 10^{-4}$ to $1 \times 10^{-2}$ M.

The stabilizing effect on PQQGDH from the inclusion of calcium ions or calcium salts can be further enhanced through the inclusion of an amino acid selected from the group consisting of glutamic acid, glutamine and lysine. One or two or more amino acids can be selected from the group consisting of glutamic acid, glutamine and lysine. Egg white albumin (OVA) can also be included.

Alternatively, PQQGDH can be stabilized through the inclusion of (1) one or two or more compounds selected from the group consisting of aspartic acid, glutamic acid, α-ketoglutaric acid, malic acid, α-ketogluconic acid, α-cyclodextrin and salts thereof and (2) albumin.

Glucose can be measured by the following methods in the present invention.

The glucose measurement reagent, glucose assay kit and glucose sensor of the present invention can be in the form of a liquid (aqueous solution, suspension, etc.), vacuum-dried or spray-dried powder or freeze-dried preparation. There are no particular limits on the method of drying, which may be an ordinary method. The composition comprising an enzyme of the present invention may be a freeze-dried product or may be a solution obtained by re-dissolving a dried product.

Glucose can be measured by the following methods in the present invention.

Glucose Measurement Reagent

The glucose measurement reagent of the present invention typically includes GDH, buffers, mediators and other reagents necessary for measurement, a glucose standard solution for preparing the calibration curve, and directions for use. The kit of the present invention can be provided for example as a freeze-dried reagent or as a solution in a suitable storage solution. Preferably the GDH of the present invention is provided in holoenzyme form, but it can also be provided in apoenzyme form and converted to holoenzyme form for use.

Glucose Assay Kit

The present invention is characterized by the glucose assay kit comprising the PQQGDH according to the present invention. The glucose assay kit of the present invention contains the PQQGDH according to the present invention in the amount enough to assay at least once. Typically, the kit contains the buffer required for the assay, a mediator, glucose standard solutions for making a calibration curve and instructions for the use in addition to the PQQGDH of the present invention. The PQQGDH according to the present invention can be provided in various forms, e.g., as a frozen and dried reagent or a solution in an appropriate storage solution. Preferably, the PQQGDH of the present invention is provided as a holoenzyme, but can be provided as an apoenzyme and converted into the holoenzyme at use.

Glucose Sensor

The present invention is characterized by the glucose sensor comprising the PQQGDH according to the present invention. As an electrode, a carbon electrode, a gold electrode or a platinum electrode is used, and the enzyme of the present invention is immobilized on this electrode. As immobilization methods, there are the method of using a crosslinking reagent, the method of including in macromolecular matrix, the method of coating with a dialysis membrane, an optical crosslinking polymer, a conductive polymer, and a redox polymer. Alternatively, the enzyme may be immobilized in the polymer or absorbed/immobilized on the electrode with an electronic mediator typified by ferrocene or derivatives thereof. Or these may be used in combination. Preferably, the PQQGDH of the present invention is immobilized on the electrode as the holoenzyme, but can be immobilized in the apoenzyme form and PQQ can be provided as another layer or in another solution. Typically, the PQQGDH of the present invention is immobilized on the carbon electrode using glutaraldehyde, and subsequently glutaraldehyde is blocked by treating with a reagent having an amine group.

The glucose concentration can also be measured as follows. The buffer is placed in a thermostatic cell, the mediator are added, and the temperature is kept constant. As an action electrode, the electrode on which the PQQGDH has been immobilized is used, and a counter electrode (e.g., platinum electrode) and a reference electrode (e.g., Ag/AgCl electrode) are used. A constant voltage is applied to the carbon electrode, after a current becomes a steady state, a sample containing glucose is added and an increase of the current is measured. The glucose concentration in the sample can be calculated in accordance with the calibration curve made by the glucose solutions with standard concentrations.

DESCRIPTION OF THE PREFERRED EMBODIMENTS

The present invention is explained in more detail below using examples.

EXAMPLE 1

Construction of Plasmid Expressing PQQ-dependent Glucose Dehydrogenase Gene

The wild-type PQQ-dependent glucose dehydrogenase gene-expression plasmid pNPG5 comprises a structural gene coding for PQQ-dependent glucose dehydrogenase derived from *Acinetobacter baumanni* strain NCIMB11517 inserted into the multicloning site of the pBluescript SK(-) vector. Its nucleotide sequence is represented by SEQ ID NO 2 in the sequence tables, while the amino acid sequence of PQQ-dependent glucose dehydrogenase as predicted from that nucleotide sequence is represented by SEQ ID NO 1 in the sequence tables.

5 μg of pNPG5 DNA was cleaved with the restriction enzymes BamHI and XhoI (Toyo Boseki) to isolate the structural gene part of mutant PQQ-dependent glucose dehydrogenase. The isolated DNA was reacted for 16 hours at 16° C. with pTM33 (1 μg) cleaved with BamHI and XhoI and one unit of T4 DNA ligase to ligate the DNA. The ligated DNA was used to transform competent cells of *E. coli* DH5α. The resulting expression plasmid was named pNPG6.

EXAMPLE 2

Preparation of *Pseudomonas* Bacterial Transformant

*Pseudomonas putida* TE3493 (Fermentation Research Institute Deposit No. 12298) was cultured for 16 hours at 30° C. in LBG medium (LB medium+0.3% glycerol), the cell bodies were collected by centrifugation (12,000 rpm, 10 minutes), and 8 ml of ice-cooled 5 mM K-phosphate buffer (pH 7.0) comprising 300 mM sucrose was added and the cells were suspended. The cells were collected by further centrifugation (12,000 rpm, 10 minutes), and 0.4 ml of ice-cooled 5 mM K-phosphate buffer (pH 7.0) comprising 300 mM sucrose was added thereto and the cells were suspended.

0.5 μg of the pNPG6 expression plasmid obtained in Example 1 was added to this suspension, and the cells were transformed by electroporation. The target transformant was obtained from a colony grown on LB agar medium comprising 100 μg/ml streptomycin.

EXAMPLE 3

Preparation of PQQ-dependent GDH Sample 500 ml of Terrific broth was dispensed into a 2L Sakaguchi flask, autoclaved at 121° C. for 20 minutes and left to cool, after which separately sterile-filtered streptomycin was added to 100 μg/ml. 5 ml of culture liquid of *Pseudomonas putida* TE3493 (pNPG6) which had been cultured in advance for 24 hours at 30° C. in PY medium comprising 100 μg/ml streptomycin was seeded in this medium, and cultured by aeration-agitation for 40 hours at 30° C. After completion of culture, PQQ-dependent glucose dehydrogenase activity was about 30 U/ml per 1 ml of culture liquid according to the activity measurement described above.

The aforementioned cell bodies were collected by centrifugation, suspended in 20 mM phosphate buffer (pH 7.0), disrupted by ultrasound treatment and centrifuged again to obtain a supernatant which was the raw enzyme liquid. The resulting raw enzyme liquid was isolated and purified by HiTrap-SP (Amersham Pharmacia) ion-exchange column chromatography. This was then dialyzed with 10 mM PIPES-NaOH buffer (pH 6.5), and calcium chloride was added to a final concentration of 1 mM. Finally, it was isolated and purified by HiTrap-DEAE (Amersham Pharmacia) ion-exchange column chromatography to obtain a purified enzyme sample. The sample obtained by this method exhibited a roughly single band in SDS-PAGE.

The purified enzyme obtained in this way was used as the PQQ-dependent GDH evaluation sample.

EXAMPLE 4

Preparation of NAD-dependent GDH Sample

A commercial product (GLD-311) sold by Toyo Boseki was obtained and used as the NAD-dependent GDH sample.

EXAMPLE 5

Preparation of FAD-dependent GDH Sample

Using an *Aspergillus terreus* subspecies and *Penicillium lilacinoechinulatum* NBRC6231 (purchased from the National Institute of Technology and Evaluation) as the FAD-dependent GDH-producing organisms, the respective L dried samples were seeded on potato dextrose agar medium (Difco) and restored by incubation at 25° C. The hyphae on the restored plates were collected together with the agar and suspended in filter-sterilized water. 6 L of production medium (1% wheat germ extract, 1.5% soy peptides, 0.1% $MgSO_4$ heptahydrate, 2% glucose, pH 6.5) was prepared in two 10 L jar fermenters, and after 15 minutes of autoclave sterilization at 120° C., the aforementioned respective hyphal suspensions were added to initiate culture. The culture conditions were temperature 30° C., aeration 2 L/minute, agitation 380 rpm. Culture was stopped after 64 hours, and cells of the respective strains were separately collected on filter paper by suction filtration using a Nutsche filter. 5 L of culture liquid was concentrated to 1/10 volume using a hollow fiber module for ultrafiltration with a molecular weight cut-off of 10,000 and ammonium sulfate was added to a final concentration of 60% saturation (456 g/L) to dissolve each concentrate. This was then centrifuged for 15 minutes at 8000 rpm in a Hitachi high-speed cooled centrifuge to precipitate the residue, the supernatant was adsorbed by an Octyl-Sepharose column and gradient eluted at an ammonium sulfate concentration of 0.6 to 0.0 saturation to collect a fraction having GDH activity. The resulting GDH solution was gel filtered with a G-25 Sepharose column and desalted by collecting the protein fraction, and ammonium sulfate equivalent to 0.6 saturation was added and dissolved in the desalted liquid. This was adsorbed by a Phenyl-Sepharose column, and gradient eluted at an ammonium sulfate concentration of 0.6 to 0.0 saturation to collect a fraction having GDH activity. The resulting GDH solution was further filtered with a G-25 Sepharose column to collect the protein fraction, and the resulting purified enzyme was used as the FAD-dependent GDH evaluation sample.

The mediator used in the composition for glucose measurement, glucose assay kit, glucose sensor or glucose measurement method of the present invention is not particularly limited, but preferably 2,6-dichlorophenol-indophenol (abbrev. DCPIP), ferrocene or derivatives of these (such as potassium ferricyanide, phenazine methosulfate or the like) can be used. These mediators can be obtained commercially.

TEST EXAMPLE 1

Method for Measuring PQQ-dependent GDH Activity

In the present invention, PQQ-dependent GDH activity is measured under the following conditions.

Measurement Principles

D-glucose+PMS+PQQGDH→D-glucono-1,5-lactone+PMS (red) PMS (red)+DCPIP→PMS+DCPIP (red)

The presence of DCPIP (red) formed by reduction of 2,6-dichlorophenol-indophenol (DCPIP) with phenazine methosulfate (PMS) (red) was measured by spectrometry at 600 nm. To investigate substrate specificity, the D-glucose part was replaced with another sugar, and specificity for their respective substrates was measured.

Definition of Units 1 unit signifies the amount of PQQGDH enzyme needed to form 1.0 micromole of DCPIP (red) per minute under the conditions described below.

Methods

A. D-glucose solution: 1.0 M (1.8 g D-glucose (molecular weight 180.16)/10 mL $H_2O$)
B. PIPES-NaOH solution, pH 6.5 : 50 mM (1.51 g of PIPES (molecular weight 302.36) suspended in 60 mL of water with pH adjusted to 6.5±0.05 at 25° C. using 5N NaOH and water added to a total of 100 ml)
C. PMS solution: 24 mM (73.52 mg phenazine methosulfate (molecular weight 817.65)/10 ml $H_2O$)
D. 50 mM PIPES buffer pH 6.5 (comprising 0.1% Triton X-100)
E. Enzyme diluent: 50 mM PIPES buffer pH 6.5 (comprising 1 mM calcium chloride, 0.1% Triton X-100, and 0.1% BSA)

Procedure:

1. The following reaction mixture was prepared in a light-protected bottle and stored on ice (prepared at the time of use).
   4.5 ml D-glucose solution (A)
   21.9 ml PIPES-NaOH solution (pH6.5)(B)
   2.0 ml PMS solution (C)
   1.0 ml DCPIP solution (D)
   The concentrations in this assay mixture were as follows:
   PIPES buffer: 36 mM
   D-glucose: 148 mM
   PMS: 1.58 mM
   DCPIP: 0.066 mM 3.0 ml of the reaction mixture were placed in a test tube (plastic) and pre-warmed for 5 minutes at 37° C.

0.1 ml of enzyme solution was added followed by inverting gently to mix.

The reduction in the absorbance relative to water at 600 nm was recorded for 4 to 5 minutes with a spectrophotometer while maintaining the temperature of the mixture at 37° C., and the ΔOD per minute was calculated from the initial linear portion of the curve (OD test).

At the same time, the same procedure was repeated with the exception of adding enzyme diluent (E) instead of enzyme solution followed by measurement of the blank (ΔOD blank).

Enzyme powder was dissolved with cold enzyme diluent (E) immediately prior to the assay, and then diluted to 0.05 to 0.10 U/ml with the same buffer (the use of plastic tubes is preferable to ensure adhesion of the enzyme).

To evaluate substrate specificity, the above activity measurement operation was performed using as the substrate a solution of another sugar in place of the glucose solution Calculations:

Activity was calculated using the following formula.

$$U/ml = \{\Delta OD/min(\Delta OD\ test - \Delta OD\ blank) \times Vt \times df\} / (16.8 \times 1.0 \times Vs)$$

U/mg=(U/ml)×1/C
Vt=Total volume (3.1 ml)
Vs=Sample volume (0.1 ml)
16.8: Millimolar molecular absorption coefficient of DCPIP under the above-mentioned measurement conditions ($cm^2/\mu M$)
1.0: Path length (cm)
df: Dilution factor
C: Enzyme concentration in solution (c mg/ml)

TEST EXAMPLE 2

Method for Measuring NAD-dependent GDH Activity

In the present invention, NAD-dependent GDH activity is measured under the following conditions. Glucose dehydrogenase manufactured by Toyo Boseki (GLD311) was used as the NAD-dependent GDH enzyme sample.

Measurement Principles

D-glucose+$NAD^+$→D-glucono-1,5-lactone+NADH+$H^+$

NADH production was measured by measuring changes in absorbance at 340 nm.

Definition of Units 1 unit signifies the amount of NADGDH enzyme needed to form 1.0 micromole of NADH per minute under the conditions described below.

Methods

Reagents

A. D-glucose solution: 1.5 M (2.7 g D-glucose (molecular weight 180.16)/10 mL $H_2O$)
B. Tris-HCl buffer, pH 8.0: 100 mM (1.21 g of tris(hydroxymethyl)aminomethane (molecular weight 121.14) suspended in 90 mL of water with pH adjusted to 8.0±0.05 at 25° C. using 5N HCl and water added to a total of 100 ml)
C. NAD solution: 8% (80 mg NAD (molecular weight 717.48)/1 ml $H_2O$)
D. Enzyme diluent: Potassium phosphate buffer (pH 7.2)

Procedures
1. The following reaction mixture was prepared in a light-shielded bottle, and stored on ice (as needed)
   0.9 ml D-glucose solution (A)
   7.8 ml Tris-HCl buffer (pH 8.0) (B)
   0.3 ml NAD solution (C)

The concentrations of the aforementioned assay mixtures in the reaction liquid were as follows

| | |
|---|---|
| D-glucose | 148 mM |
| Tris-HCl buffer | 77 mM |
| NAD | 0.26% |

2. 3.0 ml of reaction mixture was placed in a plastic test tube, and pre-heated for 5 minutes at 37° C.
3. 0.05 ml of enzyme solution was added, and mixed by gentle inversion.
4. Changes in absorbancy at 340 nm relative to water were recorded for 4 to 5 minutes with a spectrometer with the temperature maintained at 37° C., and the ΔOD per minute after the first appearance of a straight line on the curve was calculated (OD test).

At the same time, the same methods were repeated except that enzyme diluent (D) was added in place of the enzyme solution, and a blank measurement (ΔOD blank) was taken.

Enzyme powder was dissolved in ice-cooled enzyme diluent (D) immediately before the assay, and diluted to 0.10 to 0.70 U/mL with the same buffer (preferably using a plastic tube considering the adhesiveness of the enzyme).

To evaluate substrate specificity, the above measurement operation was performed using a solution of another sugar in place of the glucose solution.

Calculations
Activity was calculated using the following formula.

$$U/ml = \{\Delta OD/min(\Delta OD\ test - \Delta OD\ blank) \times Vt \times df\} / (6.22 \times 1.0 \times Vs)$$

$$U/mg = (U/ml) \times 1/C$$

Vt: Total volume (3.05 ml)
Vs: Sample volume (0.05 ml)
6.22: Millimolar molecular absorption coefficient of NADH (cm$^2$/micromole)
1.0 Optical path length (cm)
df: Dilution coefficient
C: Enzyme concentration in solution (c mg/ml)

TEST EXAMPLE 3

Method for Measuring FAD-dependent GDH Activity

In the present invention, FAD-dependent GDH activity was measured under the following conditions.

Reagents
50 mM PIPES buffer pH 6.5 (comprising 0.1% Triton X-100)
14 mM 2,6-dichlorophenol indophenol (DCPIP) solution
1 M D-glucose solution 15.8 ml of the aforementioned PIPES buffer, 0.2 ml of DCPIP solution and 4 ml of D-glucose were mixed to make the reaction reagent.

Measurement Conditions
2.9 ml of reaction reagent was pre-heated for 5 minutes at 37° C. 0.1 ml of GDH solution was added and slowly mixed, after which changes in absorbancy relative to water were measured for 5 minutes at 600 nm with a spectrometer kept at 37° C., and the change in absorbancy ($\Delta OD_{TEST}$) per minute beginning with the straight line was measured. In a blind test, the change in absorbancy ($\Delta OD_{BLANK}$) per minute was measured similarly with the solvent used for dissolving the GDH added to the reagent mixture in place of the GDH solution. GDH activity was calculated from these values by the following formula. One unit (U) of GDH activity here is defined as the amount of enzyme needed to reduce 1 micromole of DCPIP in 1 minute in the presence of D-glucose at a concentration of 200 mM.

$$\text{Activity (U/ml)} = \{-(\Delta OD_{TEST} - \Delta OD_{BLANK}) \times 3.0 \times \text{dilution ratio}\} / \{16.3 \times 0.1 \times 1.0\}$$

In the formula, 3.0 is the amount (ml) of reaction reagent + enzyme solution, 16.3 is the millimolar molecular absorption coefficient (cm$^2$/micromole) under these activity measurement conditions, 0.1 is the amount of enzyme solution (ml) and 1.0 is the optical light path (cm) of the cell.

Since GDH uses three different coenzymes, improvements in the heat stability of each were investigated under different conditions. For example, in the following Examples 6 to 8 an enzyme solution adjusted to 5 U/ml with pH 6.5 buffer was first heat treated for 16 hours at 50° C. in the case of PQQGDH, and surviving PQQGDH activity was compared to confirm improvement in heat stability. In the same way, in the case of NADGDH, an enzyme liquid adjusted to 85 U/ml with pH 7.2 buffer was heat treated for 1 hour at 50° C., and surviving NADGDH activity was compared to confirm improvement in heat stability. Similarly, in the case of FADGDH, an enzyme solution adjusted to 5 U/ml with pH 7.2 buffer was heated treated for 15 to 30 minutes at 50° C. or 55° C., and surviving FADGDH activity was compared to confirm improvement in heat stability.

In Examples 9 and 10 below, the pH of enzyme solutions prepared with various 50 mM buffers (0.4 to 5.1 U/ml) was observed, the solutions were heat treated for 15 minutes at 50° C. or for 30 minutes at 50° C. or for 15 minutes at 55° C. or for 30 minutes at 55° C., GDH activity was measured, and activity survival (%) was calculated. Activity survival was then compared to confirm improvements in heat stability.

EXAMPLE 6

Confirming Heat Stability Using Glucose Measurement System (1)

This was done using the methods for measuring PQQGDH activity described in Test Example 1 above. To measure the enzyme activity of PQQGDH with the apoenzyme form included, activity was also measured in a reaction mixture to which PQQ had been added with a final concentration of 860 nM.

First, 50 ml of PQQGDH dissolved to about 5.0 U/ml in the enzyme diluent (50 mM PIPES-NaOH buffer (pH 6.5) comprising 1 mM CaCl$_2$, 0.1% Triton X-100 and 0.1% BSA) was prepared. The 10× concentrations of various compounds shown in Tables 1 and 2 were then added in amounts of 0.1 ml to 0.33 ml of this enzyme solution, and the base buffers described in Tables 1 and 2 were also added to prepare two samples each with a total volume of 1.0 ml. 2 control samples were also prepared wherein 0.1 ml of distilled water was added in place of the various compounds. Of the two samples, one was stored for 16 hours at 4° C., while the other was treated for 16 hours at 50° C. After treatment, each sample was diluted 10 times with enzyme diluent, and PQQGDH activity was measured. In each case, enzyme activity after 16 hours of storage at 4° C. was given as 100, and the activity values after 16 hours of treatment at 50° C. were compared and given as relative values (%).

Improvements in heat stability were seen when each of the compounds shown in Tables 1 and 2 were included in the PQQGDH composition. Using potassium phosphate buffer as the base, the heat stability of the holo-type PQQGDH was lower when succinic acid, pimelic acid and dimethylglutaric acid were added, but this is attributed to loss of PQQ from the enzyme. Improvements in stability were seen with both the holo- and apoenzymes, and it is thought that these compounds help to maintain the three-dimensional structure of the enzyme itself.

Table 1 shows survival (%) of PQQGDH activity after 16 hours of treatment at 50° C. of PQQGDH compositions including various compounds using PIPES buffer (pH 6.5) as the base.

Table 2 shows survival (%) of PQQGDH activity after 16 hours of treatment at 50° C. of PQQGDH compositions including various compounds using phthalic acid buffer (pH 7.0), potassium phosphate buffer (pH 7.0) as the base.

TABLE 1

| | Base buffer: 10 mM PIPES (pH 6.5), 1 mM CaCl$_2$ | |
|---|---|---|
| | Apo + Holo | Holo |
| Blank (4° C., 16 hrs) | 100% | 100% |
| (50° C., 16 hrs) | 63% | 67% |
| 1% mannitol | 79% | 85% |
| 1% inositol | 87% | 91% |
| 1% D-(+)-arabitol | 79% | 82% |
| 1% adonitol (Adonit) | 84% | 87% |
| 0.2% galactitol | 79% | 85% |
| 1% L-valine | 76% | 74% |
| 0.25% L-histidine | 77% | 72% |
| 0.2% L-phenylalanine | 72% | 72% |
| 0.1% L-leucine | 70% | 70% |
| 1% inositol | 80% | 80% |
| 1% DL-calcium glycerate | 82% | 87% |

TABLE 2

| | Base buffer: 50 mM phthalic acid (pH 7.0), 0.22% Triton-X, 1 mM CaCl$_2$ | | Base buffer: 50 mM potassium phosphate (pH = 7.0), 0.22% Triton-X, 1 mM CaCl$_2$ | |
|---|---|---|---|---|
| | Apo + Holo | Holo | Apo + Holo | Holo |
| Blank | | | | |
| (4° C., 16 hrs) | 100% | 100% | 100% | 100% |
| (50° C., 16 hrs) | 50% | 17% | 16% | 10% |
| 1% succinic acid | 84% | 83% | 42% | 5% |
| 1% potassium chloride | 69% | 27% | 53% | 48% |
| 1% ammonium chloride | 84% | 57% | 58% | 48% |
| 1% diammonium hydrogen citrate | 38% | 36% | 44% | 43% |
| 1% fumaric acid | 66% | 38% | 58% | 52% |
| 1% malonic acid | 88% | 77% | 42% | 31% |
| 1% pimelic acid | 99% | 95% | 41% | 5% |
| 1% 3-3' dimethyl-glutaric acid | 99% | 94% | 29% | 5% |
| 1% L-lysine-hydrochloride | 66% | 31% | 44% | 31% |
| 1% taurine | 71% | 45% | 19% | 7% |

EXAMPLE 7

Confirming Heat Stability Using Glucose Measurement System (2)

This was done using the methods for measuring NADGH activity described in Test Example 2 above.

First, 50 ml of NADGDH (Toyo Boseki GLD-311) dissolved in enzyme diluent to about 250 U/ml was prepared. The 10× concentrations of various compounds shown in Table 3 were then 10 added in amounts of 0.1 ml to 0.33 ml of this enzyme solution, and potassium phosphate buffer (pH 7.2) was added to prepare two samples with a total volume of 1.0 ml each. 2 control samples were also prepared wherein 0.1 ml of distilled water was added in place of the various compounds.

Of the two samples, one was stored at 4° C., while the other was treated for 1 hour at 50° C. After treatment, each sample was diluted 50 times with enzyme diluent, and NADGDH activity was measured. In each case, enzyme activity after storage at 4° C. was given as 100, and the activity values after 1 hour of treatment at 50° C. were compared and given as activity survival values (%).

Effects were seen with all the dicarboxylic acids studied, and the greatest improvement in heat stability was seen when succinic acid and maleic acid were added.

Table 3 shows survival (%) of NADGDH activity after 1 hour of treatment at 50° C. of NADGDH compositions including various compounds.

TABLE 3

| | | GDH activity (U/ml) | | |
|---|---|---|---|---|
| | Added compound | Stored at 4° C. | 50° C., 1 h Heat treatment | Activity survival (%) |
| NAD-GDH | Not added | 85.9 | 71.8 | 83.6 |
| | 0.1% succinic acid | 85.5 | 82.2 | 96.2 |
| | 0.1% malonic acid | 85.7 | 76.0 | 88.7 |
| | 0.1% phthalic acid | 86.6 | 76.9 | 88.8 |
| | 0.1% maleic acid | 90.1 | 86.6 | 96.2 |
| | 0.1% glutaric acid | 85.5 | 76.7 | 89.7 |

EXAMPLE 8

Confirming Heat Stability Using Glucose Measurement System (3)

This was done using the methods for measuring FADGDH activity described in Test Example 3 above.

First, 50 ml of the FADGDH specified in Example 5 dissolved to about 10 U/ml in enzyme diluent (50 mM potassium phosphate buffer (pH 7.2)) was prepared. Two samples were prepared consisting of 0.5 ml of 1% or 0.5% BSA added to 0.5 ml of this enzyme solution, for a total volume of 1.0 ml. The respective 2× concentrations of succinic acid, malonic acid, phthalic acid, maleic acid, glutaric acid, sodium chloride, sodium sulfate, trisodium citrate, and ammonium sulfate shown in Tables 5 and 6 were prepared, and 0.5 ml of each was added in the same way to prepare two samples each with a total volume of 1.0 ml. Two control samples were also prepared wherein 0.1 ml of distilled water was added in place of the various compounds.

Of the two samples, one was stored at 40° C., while the other was treated for 30 minutes at 50° C. After treatment, each sample was diluted 21 times with enzyme diluent, and FADGDH activity was measured. In each case, enzyme activity after storage at 4° C. was given as 100, and the activity values after 1 hour of treatment at 50° C. were compared and given as activity survival values (%).

The heat stability of FAD-GDH was clearly improved by addition of the proteinaceous stabilizer (BSA) (Table 4). Improvements in the heat stability of FAD-GDH were also seen from addition of various dicarboxylic acid compounds and salt compounds, and succinic acid and malonic acid of the dicarboxylic acid compounds and sodium sulfate of the salt compounds had the greatest effect (Tables 5 and 6). In the case of succinic acid, malonic acid and sodium sulfate, it is thought that stability could be improved even by addition of a few moles. Since adequate effects were achieved even with a simple salt compound such as sodium chloride, it was discovered for the first time that in the case of FAD-GDH heat stability can be achieved simply by raising the ionic strength.

Table 4 shows survival (%) of FADGDH activity after 30 minutes of treatment at 50° C. of FADGDH compositions with a proteinaceous stabilizer included.

Table 5 shows survival (%) of FADGDH activity after 30 minutes of treatment at 50° C. of FADGDH compositions with dicarboxylic acid compounds included.

Table 6 shows survival (%) of FADGDH activity after 30 minutes of treatment at 50° C. of FADGDH compositions with salt compounds included.

TABLE 4

| | | GDH activity (U/ml) | | |
|---|---|---|---|---|
| | Added compound | Stored at 4° C. | 50° C., 0.5 h Heat treatment | Activity survival (%) |
| Aspergillus terreus-derived FAD-GDH | Not added | 5.0 | 0.6 | 12.9 |
| | 0.5% BSA | 5.1 | 1.3 | 25.5 |
| | 2.5% BSA | 5.1 | 3.0 | 57.9 |
| Penicillium NBRC6231 strain FAD-GDH | Not added | 4.3 | 0.1 | 2.8 |
| | 0.5% BSA | 4.1 | 0.2 | 4.5 |
| | 2.5% BSA | 4.1 | 0.3 | 7.4 |

TABLE 5

| | | Activity survival rate after 30 minutes of treatment at 50° C. (%) Dicarboxylic acid concentration | | | | |
|---|---|---|---|---|---|---|
| | Added compound | 0 mM | 20 mM | 50 mM | 100 mM | 200 mM |
| Aspergillus terreus-derived FAD-GDH | Succinic acid | 12.5 | 19.9 | 33.9 | 51.1 | 64.0 |
| | Malonic acid | 12.5 | 16.0 | 26.3 | 41.2 | 58.7 |
| | Phthalic acid | 12.5 | 11.5 | 14.6 | 21.1 | 35.0 |
| | Maleic acid | 12.5 | 13.0 | 17.6 | 25.8 | 40.4 |
| | Glutaric acid | 12.5 | 13.9 | 18.9 | 28.5 | 45.2 |
| Penicillium NBRC6231 strain FAD-GDH | Succinic acid | 11.1 | 26.7 | 47.8 | 69.2 | 76.3 |
| | Malonic acid | 11.1 | 21.8 | 38.9 | 59.1 | 70.6 |
| | Phthalic acid | 11.1 | 13.3 | 22.0 | 28.2 | 38.7 |
| | Maleic acid | 11.1 | 14.9 | 25.1 | 35.7 | 50.2 |
| | Glutaric acid | 11.1 | 16.0 | 28.1 | 43.7 | 59.7 |

TABLE 6

| | | GDH activity (U/ml) | | |
|---|---|---|---|---|
| | Added compound | Stored at 4° C. | 50° C., 15 min Heat treatment | Activity survival (%) |
| Aspergillus terreus- | Not added | 5.1 | 0.8 | 15.8 |
| | 20 mM sodium chloride | 4.8 | 0.8 | 17.3 |

TABLE 6-continued

| | | GDH activity (U/ml) | | |
|---|---|---|---|---|
| | Added compound | Stored at 4° C. | 50° C., 15 min Heat treatment | Activity survival (%) |
| derived FAD-GDH | 20 mM sodium sulfate | 4.8 | 1 | 20.6 |
| | 20 mM trisodium citrate | 5.1 | 0.8 | 16.6 |
| | 20 mM ammonium sulfate | 5.2 | 0.9 | 18.1 |
| | 50 mM sodium chloride | 4.8 | 1 | 19.8 |
| | 50 mM sodium sulfate | 4.9 | 1.3 | 26.0 |
| | 50 mM trisodium citrate | 4.9 | 1.1 | 22.1 |
| | 50 mM ammonium sulfate | 5.1 | 1.1 | 21.7 |
| | 100 mM sodium chloride | 4.7 | 1.1 | 23.0 |
| | 100 mM sodium sulfate | 4.7 | 1.7 | 35.9 |
| | 100 mM trisodium citrate | 4.8 | 1.5 | 32.5 |
| | 100 mM ammonium sulfate | 5.2 | 1.5 | 28.1 |

EXAMPLE 9

Study of Heat Stability Improvement Effects of GDH Composition with pH Maintained in the Acid Range This was done according to the methods for measuring FADGDH activity described in Test Example 3 above.

First, 10 ml of the two kinds of FADGDH obtained in Example 5 dissolved to about 10 U/ml in enzyme diluent (50 mM potassium phosphate buffer (pH 6.5)) was prepared. 1.8 ml of 50 mM potassium phosphate buffer (pH 4.3) or 50 mM potassium phosphate buffer (pH 5.6) or 50 mM potassium phosphate buffer (pH 7.0) was added to 0.2 ml of this enzyme solution, to a total volume of 2.0 ml. When the pH values of each of the enzyme solutions were measured, they fluctuated around pH 5.6, 6.0 and 7.2. 1 ml each was dispensed to prepare 2 samples, one of which was stored at 4° C., while the other was heat treated at 50° C. After treatment, each sample was diluted 2× with enzyme diluent, and FADGDH activity was measured. In each case, enzyme activity after storage at 4° C. was given as 100%, and the GDH activity values after 15 minutes or 30 minutes of treatment at 50° C. were compared and given as GDH activity survival values (%).

As a result, it was shown that the heat stability of a composition containing FADGDH is improved by maintaining the pH of a composition containing GDH in the acid range (Table 7).

Moreover, to investigate pH conditions in more detail, the enzyme liquid was diluted 10 times with the various buffers shown in Table 8, and after pH had been confirmed by measurement these were treated for 15 minutes at 50° C., GDH activity was measured, and survival (%) was calculated.

Figure 2:
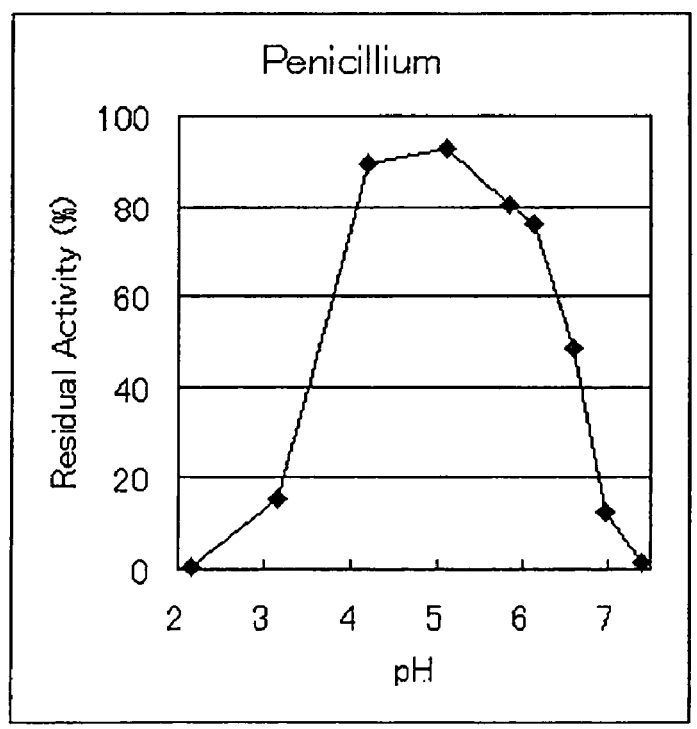
FIG. 2 shows the pH dependence of heat stability of FADGDH derived from *Penicillium lilacinoechinulatum* NBRC6231.

As a result, it was shown that heat stability was higher at a pH in the range of 3.14 to 6.97 than at 7.4 whether the composition contained FADGDH derived from the *Aspergillus terreus* subspecies or *Penillium lilacinoechinulatum* NBRC6231 (Table 8, FIG. 1, FIG. 2).

The preparation of glucose sensors and sensor chips, which are widespread applications of GDH compositions, includes a step of heat drying, and the fact that the stability of a composition containing FADGDH can be improved by maintaining its pH in the acid range is extremely important from the standpoint of improving the stability and measurement accuracy of sensor chip products which employ FADGDH.

EXAMPLE 10

Study of Improvements Achieved in Heat Stability of a GDH Composition by Including One or More Salt Compounds or Dicarboxylic Acids in a GDH Composition with the PH Maintained in the Acid Range This was done according to the methods for measuring FADGDH activity described in Test Example 3 above.

First, compound solutions were prepared consisting of sodium sulfate, trisodium citrate and ammonium sulfate each dissolved to 1 M in 50 mM potassium phosphate buffer (pH 6.5). 20 ml each of the two kinds of FADGDH obtained in Example 5 dissolved to about 10 U/ml in enzyme diluent (50 mM potassium phosphate buffer (pH 6.5)) was also prepared. 8 kinds of enzyme samples (2 ml) were then prepared consisting of each of the two kinds of FADGDH mixed 1:1 with each of the 4 kinds of compound solutions. Control enzyme liquid samples were also prepared with the pH adjusted to near 6.25 and 6.65 with 50 mM potassium phosphate buffer as controls with no compound solution added. The actual pH values of the various enzyme liquid samples were measured to confirm that the pH remained near that of the control. The enzyme liquid samples were each dispensed in 1 ml amounts to prepare two samples, one of which was stored at 4° C., while the other was heat treated for 30 minutes at 55° C. After treatment, each sample was diluted 10 times with enzyme diluent, and FADGDH activity was measured. In each case, enzyme activity after storage at 4° C. was given as 100%, and the GDH activity values after 30 minutes of treatment at 55° C. were compared and given as GDH activity survival values (%).

As a result, it was shown that greater heat stability was achieved when the pH of a composition containing GDH was maintained in the acid range and sodium sulfate, trisodium citrate, ammonium sulfate or the like was added thereto than in the case of the control enzyme liquid sample with the pH maintained in the acid range (Table 9).

Next, an equal amount of 2M sodium chloride or 1M sodium sulfate or 1M trisodium citrate or 1M ammonium sulfate was added to enzyme liquid samples (5 U/ml) consisting of the two kinds of FADGDH with the pH adjusted to 5.3 with succinic acid buffer, to prepare 8 kinds of enzyme liquid samples (2 ml). As controls with no compound solution added, control enzyme liquid samples were also prepared by 2× dilution using 50 mM sodium succinate buffer (pH 5.3). The actual pH values of the various enzyme liquid samples

TABLE 7

|  | Actual pH | Stored at 4° C. | GDH activity (U/ml) | | Activity survival (%) | |
| --- | --- | --- | --- | --- | --- | --- |
|  |  |  | 50° C., 15 min heat treatment | 50° C., 30 min heat treatment | 50° C., 15 min heat treatment | 50° C., 30 min heat treatment |
| *Aspergillus terreus*-derived FAD-GDH | 5.65 | 0.9318 | 0.7702 | 0.661 | 82.7 | 70.9 |
|  | 5.95 | 0.9302 | 0.7646 | 0.637 | 82.2 | 68.5 |
|  | 7.17 | 0.9206 | 0.1868 | 0.0337 | 20.3 | 3.7 |
| *Penicillium* NBRC6231 strain FAD-GDH | 5.59 | 0.8822 | 0.641 | 0.5916 | 72.7 | 67.1 |
|  | 5.94 | 0.8792 | 0.592 | 0.5238 | 67.3 | 59.6 |
|  | 7.17 | 0.885 | 0.051 | 0.0173 | 5.8 | 2.0 |

In 50 mM potassium phosphate buffer

TABLE 8

|  | Buffer | Actual pH | Stored at 4° C. | GDH activity 50° C., 15 min heat treatment | Activity survival (%) |
| --- | --- | --- | --- | --- | --- |
| *Aspergillus terreus*-derived FAD-GDH | Glycine-hydrochloric acid | 2.17 | 0.47 | 0.00 | 0.0 |
|  |  | 3.14 | 0.78 | 0.09 | 11.0 |
|  | Sodium acetate | 4.20 | 0.76 | 0.53 | 70.3 |
|  |  | 5.11 | 0.79 | 0.67 | 84.7 |
|  | Potassium phosphate | 5.84 | 0.84 | 0.68 | 80.9 |
|  |  | 6.12 | 0.82 | 0.62 | 76.0 |
|  |  | 6.60 | 0.81 | 0.58 | 70.9 |
|  |  | 6.97 | 0.85 | 0.38 | 45.0 |
|  |  | 7.38 | 0.82 | 0.05 | 6.6 |
| *Penicillium* NBRC6231 strain FAD-GDH | Glycine-hydrochloric acid | 2.17 | 0.57 | 0.00 | 0.7 |
|  |  | 3.14 | 0.80 | 0.12 | 15.3 |
|  | Sodium acetate | 4.20 | 0.81 | 0.72 | 89.3 |
|  |  | 5.11 | 0.82 | 0.76 | 93.0 |
|  | Potassium phosphate | 5.84 | 0.81 | 0.65 | 80.5 |
|  |  | 6.13 | 0.81 | 0.61 | 76.2 |
|  |  | 6.60 | 0.81 | 0.39 | 48.5 |
|  |  | 6.97 | 0.83 | 0.10 | 12.6 |
|  |  | 7.39 | 0.79 | 0.01 | 1.6 | were measured to confirm that the pH remained near that of the control. The enzyme liquid sample were dispensed in 1 ml amounts to prepare two samples, one of which was stored at 4° C., while the other was heat treated for 30 minutes at 55° C. After treatment, each sample was diluted 5 times with enzyme diluent, and FADGDH activity was measured. In each case, enzyme activity after storage at 4° C. was given as 100%, and the GDH activity values after 30 minutes of treatment at 55° C. were compared and given as activity survival values (%).

As a result, it was confirmed that heat stability can be improved by addition of salt compounds such as sodium chloride, sodium sulfate, trisodium citrate, ammonium sulfate and the like even at low pH values around 5. The effect seen from addition even of such an unremarkable compound as sodium chloride suggests that heat stability of an FADGDH composition can be improved by inclusion of a wide range of salt compounds (Table 10).

Since greater improvement in heat stability was achieved using the succinic acid buffer than using potassium phosphate buffer as the base, it appears that the dicarboxylic acid compound contained in the succinic acid buffer has the effect of improving heat stability in the same way as the salt compounds described above. Therefore, fluctuations in heat stability were investigated when dicarboxylic acid compounds were added with the pH of a GDH-containing composition maintained in the acid range.

First, 100 mM sodium acetate (pH 5.0) and 100 mM potassium phosphate buffer (pH 5.6) were prepared as the base buffers. 20 ml samples of the two kinds of FADGDH obtained in Example 5 dissolved to about 10 U/ml in enzyme diluent (50 mM potassium phosphate buffer (pH 6.5)) were also prepared. Next, 0.4 M succinic acid (adjusted to pH 7.0 with NaOH), 0.4 M malonic acid (adjusted to pH 7.0 with NaOH) and 0.4 M glutaric acid (adjusted to pH 7.0 with NaOH) were prepared.

0.8 ml of base buffer was mixed with 0.2 ml of enzyme liquid (10 U/ml), 1 ml of each of the various dicarboxylic acid compounds was added, and the pH of each was measured. Distilled water was also added instead of a dicarboxylic acid compound to obtain controls without a compound solution added, and the pH of each sample was adjusted to near the measurement value. The enzyme liquid samples were dispensed in 1 ml amounts to prepare two samples, one of which was stored at 4° C., while the other was heat treated at 55° C. After treatment, each sample was diluted 2 times with enzyme diluent, and FADGDH activity was measured. In each case, enzyme activity after storage at 4° C. was given as 100%, and the GDH activity values after 15 minutes or 30 minutes of treatment at 55° C. were compared and given as activity survival values (%).

As a result, it was shown that heat stability could be achieved by addition of a dicarboxylic acid such as succinic acid, malonic acid, glutaric acid or the like at a pH of around 5.5 or 6.0. These results suggest that the heat stability of a FADGDH composition can be improved by inclusion of a wide range of dicarboxylic acid compounds (Table 11).

TABLE 9

| | | | GDH activity (U/ml) | | |
| --- | --- | --- | --- | --- | --- |
| | Added compound | Actual pH | Stored at 4° C. | 55° C., 30 min heat treatment | Activity survival (%) |
| Aspergillus terreus-derived FAD-GDH | None | 6.25 | 5.1 | 0.4 | 8.7 |
| | None | 6.63 | 5.1 | 0.2 | 3.3 |
| | 0.5 M sodium sulfate | 6.43 | 5.1 | 2.4 | 47.3 |
| | 0.5 M trisodium citrate | 6.84 | 5.0 | 3.0 | 60.1 |
| | 0.5 M ammonium sulfate | 6.31 | 5.0 | 1.7 | 33.6 |
| Penicillium NBRC6231 strain FAD-GDH | None | 6.28 | 4.8 | 0.9 | 17.9 |
| | None | 6.64 | 4.8 | 0.1 | 2.0 |
| | 0.5 M sodium sulfate | 6.46 | 4.5 | 2.6 | 57.0 |
| | 0.5 M trisodium citrate | 6.87 | 4.5 | 2.5 | 56.4 |
| | 0.5 M ammonium sulfate | 6.33 | 4.6 | 3.0 | 65.0 |

In 50 mM potassium phosphate buffer

TABLE 10

| | | | GDH activity (U/ml) | | |
| --- | --- | --- | --- | --- | --- |
| | Added compound | Actual pH | Stored at 4° C. | 55° C., 30 min heat treatment | Activity survival (%) |
| Aspergillus terreus-derived FAD-GDH | None | 5.32 | 2.8 | 0.5 | 19.2 |
| | 1 M sodium chloride | 4.97 | 2.9 | 1.0 | 35.3 |
| | 0.5 M sodium sulfate | 5.02 | 2.9 | 1.9 | 63.5 |
| | 0.5 M trisodium citrate | 6.46 | 2.6 | 1.8 | 68.1 |
| | 0.5 M ammonium sulfate | 5.06 | 2.8 | 1.4 | 49.5 |
| Penicillium NBRC6231 strain FAD-GDH | None | 5.31 | 2.3 | 1.0 | 42.0 |
| | 1 M sodium chloride | 4.97 | 2.4 | 1.7 | 72.0 |
| | 0.5 M sodium sulfate | 5.02 | 2.4 | 2.1 | 87.0 |
| | 0.5 M trisodium citrate | 6.46 | 2.3 | 1.8 | 76.3 |
| | 0.5 M ammonium sulfate | 5.05 | 2.3 | 2.0 | 87.3 |

50 mM succinic acid buffer

TABLE 11

| | Added compound | Actual pH | 4° C. | GDH activity (U/ml) 55° 15 min | 55° C. 30 min | Activity survival (%) 55° 15 min | 55° C. 30 min |
|---|---|---|---|---|---|---|---|
| *Aspergillus terreus*-derived FAD-GDH | None | 5.62*[1] | 0.87 | 0.39 | 0.13 | 45.0 | 14.4 |
| | 0.2M succinic acid | 5.43*[1] | 0.82 | 0.44 | 0.22 | 52.9 | 26.5 |
| | 0.2M malonic acid | 5.67*[1] | 0.83 | 0.43 | 0.22 | 52.2 | 26.9 |
| | 0.2M glutaric acid | 5.52*[1] | 0.81 | 0.42 | 0.21 | 51.8 | 26.0 |
| | None | 6.12*[2] | 0.81 | 0.27 | 0.09 | 33.6 | 11.3 |
| | 0.2M succinic acid | 5.99*[2] | 0.83 | 0.39 | 0.18 | 46.6 | 21.4 |
| | 0.2M malonic acid | 6.19*[2] | 0.81 | 0.30 | 0.11 | 37.0 | 13.7 |
| | 0.2M glutaric acid | 6.13*[2] | 0.81 | 0.31 | 0.12 | 37.8 | 14.6 |
| *Penicillium* NBRC6231 strain FAD-GDH | None | 5.62*[1] | 0.84 | 0.47 | 0.26 | 55.2 | 30.6 |
| | 0.2M succinic acid | 5.43*[1] | 0.82 | 0.57 | 0.42 | 69.6 | 50.7 |
| | 0.2M malonic acid | 5.67*[1] | 0.82 | 0.54 | 0.37 | 65.9 | 44.7 |
| | 0.2M glutaric acid | 5.52*[1] | 0.82 | 0.56 | 0.39 | 68.0 | 47.7 |
| | None | 6.12*[2] | 0.81 | 0.18 | 0.05 | 22.7 | 5.9 |
| | 0.2M succinic acid | 5.99*[2] | 0.81 | 0.41 | 0.23 | 51.1 | 28.8 |
| | 0.2M malonic acid | 6.19*[2] | 0.81 | 0.27 | 0.11 | 33.0 | 13.4 |
| | 0.2M glutaric acid | 6.13*[2] | 0.80 | 0.30 | 0.13 | 37.0 | 16.2 |

*[1]sodium acetate buffer
*[2]potassium phosphate buffer

EXAMPLE 11

Confirmation of Storage Stability Using Glucose Measurement System

This was done according to the measurement method for PQQGDH activity described in Test Example 1 above. To measure enzyme activity of PQQGDH in the apoenzyme form as well, the activity of a reaction mixture with PQQ added to a final concentration of 860 nM was measured.

First, 10 ml of PQQGDH dissolved to about 10 U/ml in enzyme diluent (1 mM $CaCl_2$, 50 mM PIPES-NaOH buffer (pH 6.5)) was prepared. Three samples each were prepared consisting of 0.06 ml of each of the 10× concentrations of various compounds given in Table 12 added to 0.54 ml of this enzyme solution to a total volume of 0.6 ml. three control samples were also prepared having 0.06 ml of distilled water added instead of the various compounds.

After the prepared vials had been freeze dried (FDR) and the water content completely evaporated, the activity of the control vials was measured immediately. The specimen vials were first treated for 6 hours at 25° C., humidity 70%, and then stored at 37° C., and surviving activity was measured after 1 or 2 weeks. Given 100% as the activity value immediately after freeze-drying, the activity survival of each specimen was calculated as a percentage of this value. Storage stability was judged to be greater the higher the activity survival.

Addition of succinic acid, ammonium chloride, malonic acid and the like inhibited the holoenzyme conversion rate from declining, and improved powder stability. Comparing the conditions of the powders with and without added compounds, with addition the powder was more compact, and could easily be predicted to have greater resistance to moisture absorption. For reasons of supply there were limits on the kinds of carboxylic acid-containing compounds that could be used in this study, but it is thought that a wide range of other compounds would have the same effects. Since changes in powder form are thought to be associated with increased storage stability, it is also believed that the same effects could be achieved with NAD-GDH and FAD-GDH.

TABLE 12

| PQQ-GDH activity | Added compound | Activity survival (%) After FDR | 37° C. 1 w | 37° C. 2 w | Holoenzyme conversion rate (%) After FDR | 37° C. 1 w | 37° C. 2 w |
|---|---|---|---|---|---|---|---|
| 10 U/ml 600 ul/bottle (6U-T) | Water | 100.0 | 46.5 | 33.4 | 91.2 | 59.5 | 52.2 |
| | 0.01% succinic acid | 100.0 | 53.7 | 65.7 | 91.8 | 75.3 | 82.2 |
| | 0.01% ammonium chloride | 100.0 | 53.0 | 37.8 | 81.8 | 74.8 | 80.4 |
| | 0.01% malonic acid | 100.0 | 95.1 | 59.5 | 91.5 | 86.2 | 78.5 |

With the improved heat stability achieved by the present invention, it is possible to improve the storage stability and measurement accuracy of glucose measurement reagents, glucose assay kits and glucose sensors.

What is claimed is:

1. A method for preparing a glucose sensor comprising (a) combining bovine serum albumin in a composition comprising soluble flavin-bound glucose dehydrogenase (GDH), thereby improving the heat stability of GDH over that achieved without the inclusion of the bovine serum albumin, and (b) heat drying the composition onto the surface of the glucose sensor.

2. The method according to claim 1, wherein the concentration of bovine serum albumin is 0.1% by weight or more after combining bovine serum albumin with the composition comprising soluble flavin-bound glucose dehydrogenase and before heat drying the composition.

3. A glucose sensor prepared by the method of claim 1.

4. A method of measuring glucose concentration using the glucose sensor of claim 3.

5. A glucose sensor prepared by the method of claim 2.

6. A method of measuring glucose concentration using the glucose sensor of claim 5.

* * * * *

SEQUENCE LISTING

<160> NUMBER OF SEQ ID NOS: 2

<210> SEQ ID NO 1
<211> LENGTH: 455
<212> TYPE: PRT
<213> ORGANISM: Acinetobacter baumannii NCIMB11517

<400> SEQUENCE: 1

```
Asp Ile Pro Leu Thr Pro Ala Gln Phe Ala Lys Ala Lys Thr Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Val Ser Gly Ser Ala Lys Thr Val Phe
    50                  55                  60

Gln Val Pro Glu Ile Val Ser Asp Ala Asp Gly Gln Asn Gly Leu Leu
65                  70                  75                  80

Gly Phe Ala Phe His Pro Asp Phe Lys His Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Thr Thr Asp Thr Phe
        115                 120                 125

Glu Lys Pro Ile Asp Leu Ile Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Ser Lys Asp Tyr
            180                 185                 190

His Thr Tyr Met Gly Lys Val Leu Arg Leu Asn Leu Asp Gly Ser Val
        195                 200                 205

Pro Lys Asp Asn Pro Ser Phe Asn Gly Val Val Ser His Ile Tyr Thr
    210                 215                 220

Leu Gly His Arg Asn Pro Gln Gly Leu Ala Phe Ala Pro Asn Gly Lys
225                 230                 235                 240

Leu Leu Gln Ser Glu Gln Gly Pro Asn Ser Asp Asp Glu Ile Asn Leu
                245                 250                 255

Val Leu Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Thr Asn Lys
        275                 280                 285

Ser Gln Ile Lys Asp Leu Ala Gln Asn Gly Ile Lys Val Ala Thr Gly
    290                 295                 300

Val Pro Val Thr Lys Glu Ser Glu Trp Thr Gly Lys Asn Phe Val Pro
305                 310                 315                 320

Pro Leu Lys Thr Leu Tyr Thr Val Gln Asp Thr Tyr Asn Tyr Asn Asp
                325                 330                 335
```

```
Pro Thr Cys Gly Glu Met Ala Tyr Ile Cys Trp Pro Thr Val Ala Pro
            340                 345                 350

Ser Ser Ala Tyr Val Tyr Thr Gly Gly Lys Lys Ala Ile Pro Gly Trp
            355                 360                 365

Glu Asn Thr Leu Leu Val Pro Ser Leu Lys Arg Gly Val Ile Phe Arg
            370                 375                 380

Ile Lys Leu Asp Pro Thr Tyr Ser Thr Thr Leu Asp Asp Ala Ile Pro
385                 390                 395                 400

Met Phe Lys Ser Asn Asn Arg Tyr Arg Asp Val Ile Ala Ser Pro Glu
                405                 410                 415

Gly Asn Thr Leu Tyr Val Leu Thr Asp Thr Ala Gly Asn Val Gln Lys
            420                 425                 430

Asp Asp Gly Ser Val Thr His Thr Leu Glu Asn Pro Gly Ser Leu Ile
            435                 440                 445

Lys Phe Thr Tyr Asn Gly Lys
    450                 455

<210> SEQ ID NO 2
<211> LENGTH: 1368
<212> TYPE: DNA
<213> ORGANISM: Acinetobacter baumannii NCIMB11517

<400> SEQUENCE: 2 gatataccte tgacacctgc tcagttcgca aaagcgaaaa cagaaaattt tgataaaaaa      60
gtgattctgt ccaatttaaa taaaccacat gctttgttat ggggggccaga taatcaaatt     120 tggttaaccg aacgtgcaac tggcaaaatt ttaagagtaa atcctgtatc tggtagcgcg     180
aaaacagtat ttcaggttcc tgaaattgtg agtgatgctg atgggcaaaa tggtttgtta     240
ggttttgctt ttcatcctga ctttaaacat aacccttata tctatatttc aggcactttt     300
aaaaatccaa aatctacaga taagagtta cctaatcaga cgattattcg tagatatacc     360
tataataaaa ctacagatac atttgaaaag cctattgatt tgattgcagg tttaccgtca     420
tcaaaagatc atcagtctgg tcgtctcgtt attggtccag accaaaaaat ctactatacg     480
attggtgacc aaggtcgtaa tcagttagct tatctgttct taccgaatca ggcacagcat     540
actccgactc agcaagagct caatagtaaa gactaccata catatatggg taaagtatta     600
cgcttaaatc tggacggcag tgtacctaaa gacaacccaa gctttaacgg cgtagtgagt     660
catatctaca ctttagggca ccgtaatcca caaggtttag catttgcccc aaatggaaag     720
cttttacaat ctgagcaagg accaaattct gatgatgaaa ttaaccttgt attaaaaggt     780
ggtaactatg ctggccaaa tgtagctggt tataaagatg acagtggtta tgcctatgca     840
aactattcgg cagcaaccaa taatcacaa attaaagatt tagctcaaaa cgggataaaa     900
gtagcaacag tgttcctgt gactaaagag tctgaatgga ctggtaaaaa ctttgtgccg     960
cctttgaaaa ctttatatac ggtacaagat acctataact ataatgaccc tacttgtggt    1020
gagatggcat atatttgctg gccaacggtt gcaccgtcat cagcatatgt atatacggga    1080
ggcaaaaaag cgattccagg gtgggaaaat acattattgg tcccatcttt aaaacgtggg    1140
gtgattttcc gtattaaatt ggacccgaca tatagcacga ctttggatga tgctatccca    1200
atgtttaaaa gcaataaccg ttatcgtgat gtcatcgcta gtccagaagg taatacctta    1260
tatgtgctga ctgatacagc ggggaatgta caaaaagatg atggttctgt cactcatact    1320
ttagagaatc ccggttctct cattaaattt acatataacg gtaagtaa                  1368
```